United States Patent [19]
Poffenbarger

[11] Patent Number: 5,953,113
[45] Date of Patent: Sep. 14, 1999

[54] DEVICE AND METHOD FOR DETECTING, CHARACTERIZING AND CORRECTING FLAWS IN OPTIC FIBER

[76] Inventor: Steven Lewis Poffenbarger, 38 Virginia Ave., Germantown, Ohio 45327

[21] Appl. No.: 08/960,028

[22] Filed: Oct. 29, 1997

[51] Int. Cl.[6] ....................................................... G01N 21/84
[52] U.S. Cl. ........................................... 356/73.1; 356/430
[58] Field of Search .................................... 356/73.1, 430, 356/429, 389

[56] References Cited

U.S. PATENT DOCUMENTS

| | | | |
|---|---|---|---|
| 3,599,223 | 8/1971 | Bridenbaugh et al. | 356/430 X |
| 4,924,087 | 5/1990 | Bailey et al. | 356/73.1 |
| 5,410,396 | 4/1995 | Rochester | 356/73.1 |

*Primary Examiner*—Robert H. Kim
*Assistant Examiner*—Tu T. Nguyen
*Attorney, Agent, or Firm*—R. William Graham

[57] ABSTRACT

A device for use in detecting, characterizing and correcting flaws in optic fibers includes a light source for generating a beam of light at an optic fiber, a detector measurer for detectably measuring at least one of refracted light rays, diffracted light rays and scattered light rays from the beam and generating a signal in response thereto, a computer-based device operatively associated with the detector measurer for receiving the signal and manipulating the signal to produce an output indicating one of a normal area and a flawed area, a camera device operatively associated with the computer-based device and responsive to the output for visually recording the flawed area in response to indication of a flawed area and permitting display of thereof. Also, a method provided includes the steps of directing a beam of light at an optic fiber, detectably measuring at least one of refracted light rays, diffracted light rays and scattered light rays from the beam and generating a signal in response thereto, employing a computer-based device for receiving the signal and manipulating the signal to produce an output indicative of one of a normal area and flawed area, and employing a camera for recording the flawed area in response to indication of the flawed fiber. The method further includes the steps of displaying the flawed area and removing the flawed area from the fiber.

8 Claims, 3 Drawing Sheets

DEVICE AND METHOD FOR DETECTING, CHARACTERIZING AND CORRECTING FLAWS IN OPTIC FIBER

BACKGROUND OF THE INVENTION

1. Field of the Invention

The present invention relates to detecting, characterizing and correcting flaws in fiber optics. More particularly, but not by way of limitation, the invention relates to a device and method for use in detecting, characterizing and correcting flaws in optic fiber in a continuous process using a high speed vision camera and a light beam detector measuring device in combination to gain a more accurate assessment of the type and size of flaws in addition to maintaining high speed detection of flaws in the optic fiber.

2. Related Art

Optic fibers typically include an glass fiber including a core and cladding each having different indices of refraction. This glass fiber is then coated with an acrylate or a plastic like coating to protect the fiber and ensure good mechanical properties. Flaws can occur within the fiber, such as bubbles, breaks, coating delamination or surface flaws of lumps, neck downs, surface contamination, and the like. All of these negatively impact the performance of the a signal which passes through the optic fiber.

It has therefore been of continuous concern that these defects be minimized. In order to do so, devices have been made to detect a defect in the fiber. Such devices are of the type described in U.S. Pat. No. 5,436,719 to Doles et al. which discloses a laser based device for detecting when flaws occur in the optic fiber via using light which scattered into an in-plane scattered segment when the fiber is normal and which are scattered into an out-of-plane scattered segment when a defect is noticed in the fiber.

These defects can be removed from the fiber by using splicing techniques. In the fiber forming process, the length of the formed fiber is accurately recorded as it is drawn on a tower which enables the defective region to be identified. Visual inspection and microscopes have also been employed to assure removal of the defective region detected in the fiber. This is a very time consuming process. In many instances, manufactures simply hedge to the side of security in removing undamaged fiber which surrounds the defect. This results in great waste.

Accordingly, there remains a need to improve detection, characterization and correction of flaws in optic fibers. There is a need to maintain high speed of production of optic fibers with the ability to efficiently detect, characterize and correct defects in such fibers.

BRIEF SUMMARY OF THE INVENTION

It is an object to improve detection of flaws in optic fibers.

It is another object to improve characterization of flaws in optic fibers.

It is yet another object to improve correction of flaws in optic fibers.

It is still another object to increase the efficiency in which flaws are removed from optic fibers and reduce scrap.

It is another object to detect and characterize flaws at relatively high speeds.

Accordingly, the present invention calls for a device for use in detecting, characterizing and correcting flaws in optic fibers. The device includes a light source for generating a beam of light at an optic fiber, means for detectably measuring at least one of refracted light rays, diffracted light rays and scattered light rays from the beam and generating a signal in response thereto, a computer based device operatively associated with the detectably measuring means for receiving the signal and manipulating the signal to produce an output indicating one of a normal area and a flawed area, camera means operatively associated with the computer based means and responsive to the output for visually recording the flawed area in response to indication of a flawed area. The camera means includes at lease one light source and at least one high speed camera.

A method of the invention includes the steps of directing a beam of light at an optic fiber, detectably measuring at least one of refracted light rays, diffracted light rays and scattered light rays from the beam and generating a signal in response thereto, employing a computer-based device for receiving the signal and manipulating the signal and producing an output indicative of one of a normal area and a flawed area, and employing camera means for recording the flawed area in response to indication of the flawed area. The method further includes the steps of displaying the flawed area and removing the flawed area from the fiber.

Other objects and advantages will be readily apparent to those skilled in the art upon viewing the drawings and reading the detailed description hereafter.

BRIEF DESCRIPTION OF THE DRAWINGS

FIG. 1a shows an enlarged view of a part of an embodiment of the present invention.

DETAILED DESCRIPTION OF THE INVENTION

Figure 1:
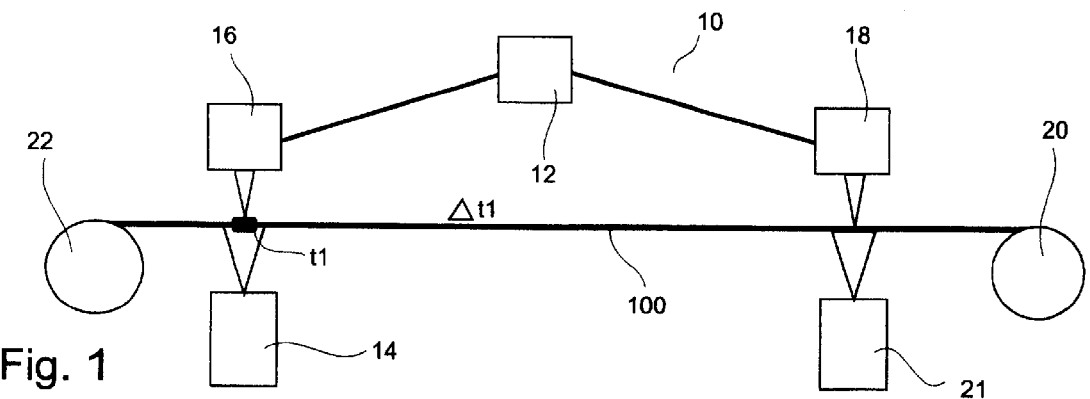
FIG. 1 is schematic block diagram of the present invention showing a flaw in the fiber at time t1.
Figure 2:
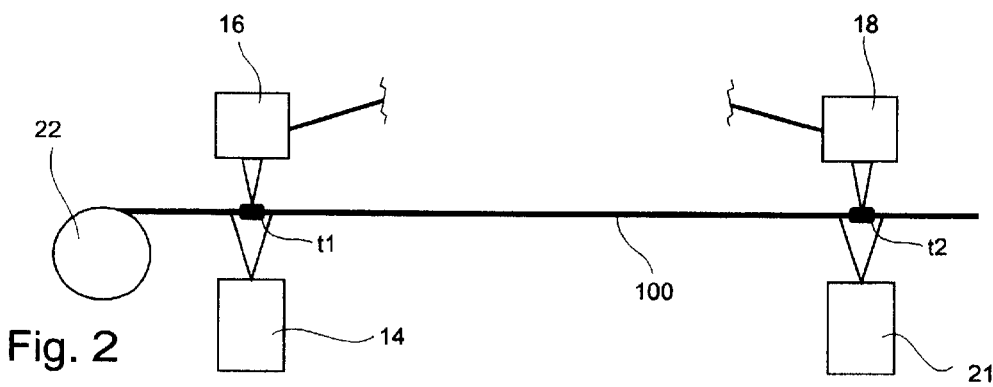
FIG. 2 is schematic block diagram of the present invention showing the flaw in the fiber at time t2.
Figure 3:
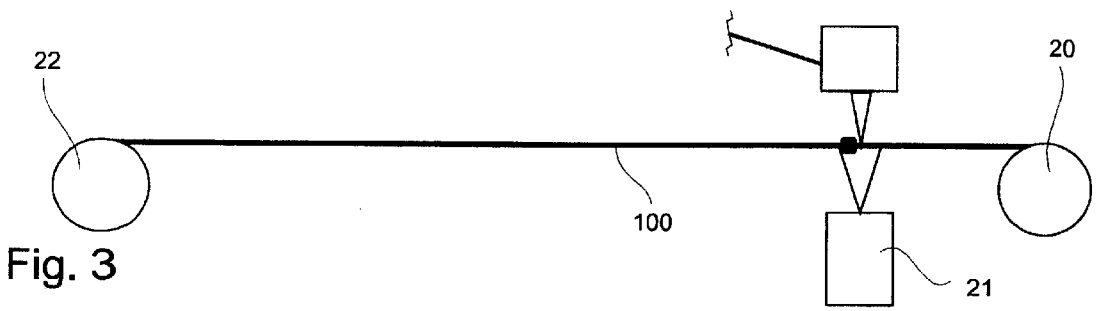
FIG. 3 is schematic block diagram of the present invention showing the flaw in the fiber at time t3.
Figure 4:
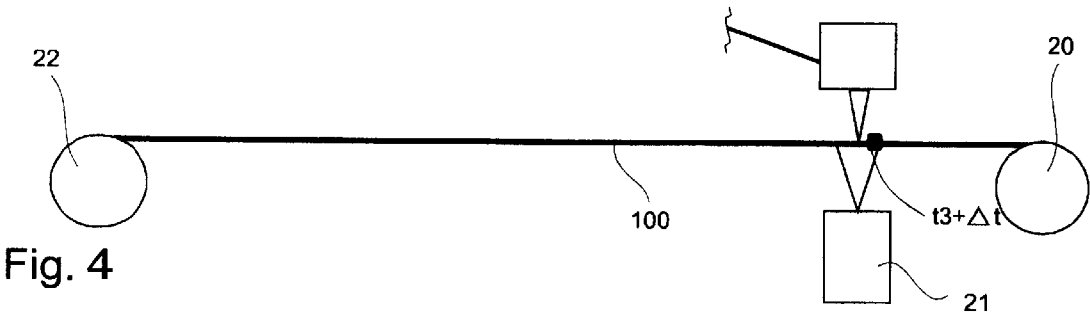
FIG. 4 is schematic block diagram of the present invention showing the flaw in the fiber at time t3+Δt.
Figure 5:
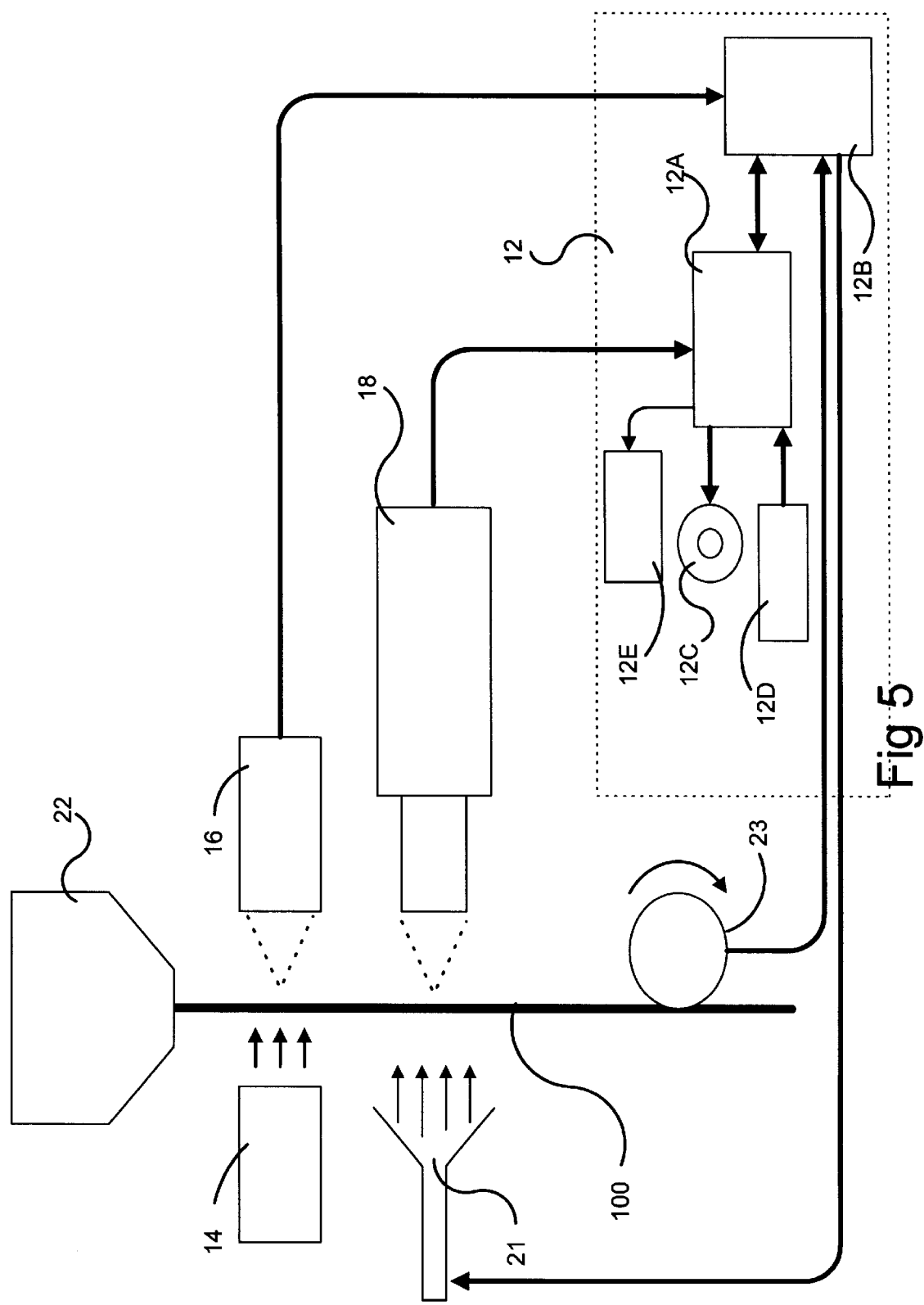
FIG. 5 shows a diagram of the present invention.
Figure 6:
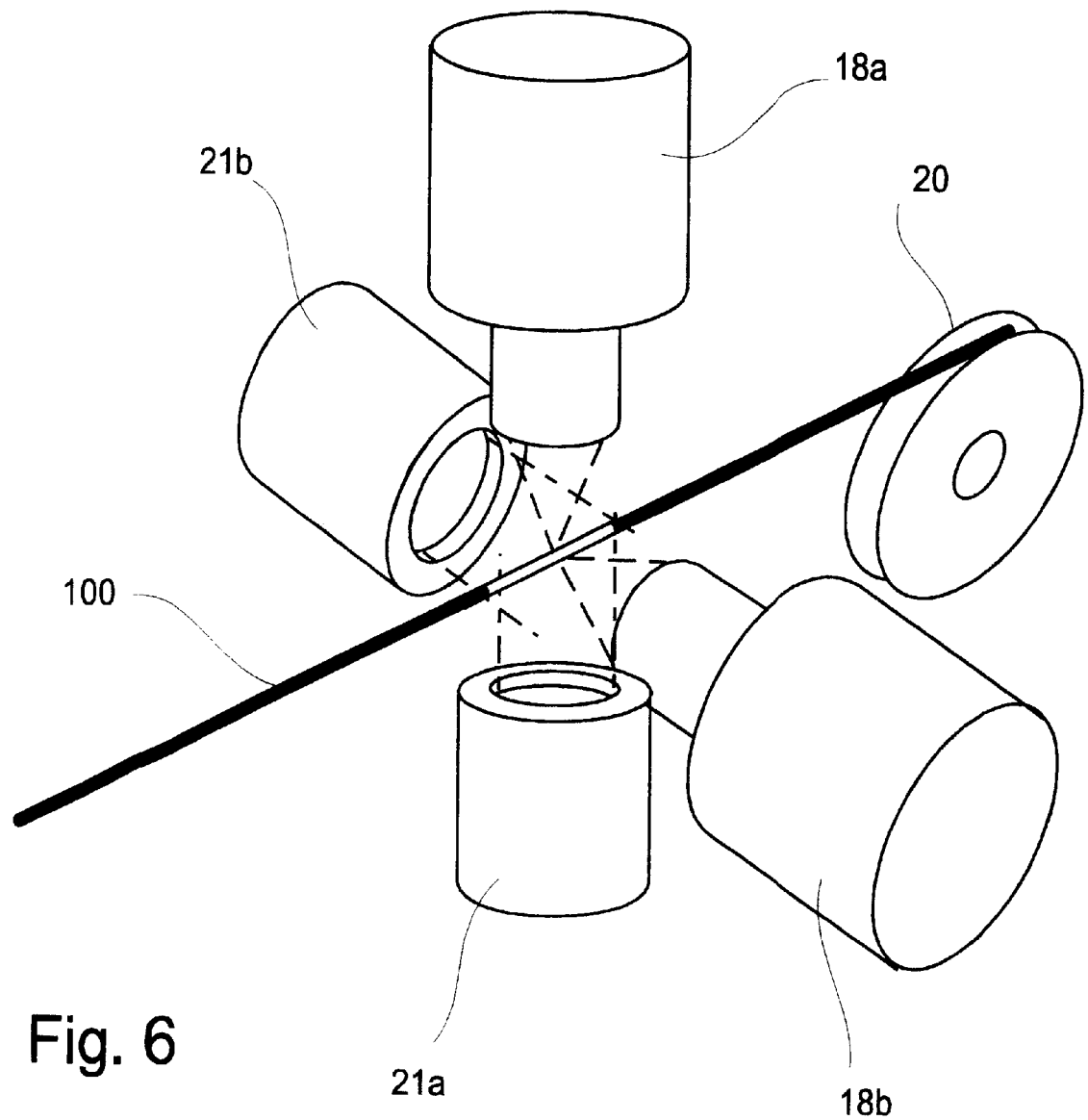
FIG. 6 shows another embodiment of the present invention.

Referring now to the drawing, the device for detection, characterization and correction of flaws in an optic fiber 100 of present invention is generally referred to by the numeral 10. The device 10 includes a computer 12, a light source 14 for generating a beam of light rays at the optic fiber 100, a detector measurer 16 operably positioned across from the light source 14 with the optic fiber 100 therebetween to receive light rays which pass thereby and which is operably connected to the computer 12. The device 10 further includes a light source 21 for generating a wide beam of light rays at the optic fiber 100 and a camera 18 operably connected to the computer 12 and positioned across from the light source 21 to record the characterization of flaws in the optic fiber 100 after detection. The light source 14, detector measurer16, camera 18 and light source 21 are operably positioned adjacent a draw tower 22.

The light source 14 and detector measurer 16 are preferably of the type described in U.S. Pat. No. 5,436,719 to Doles et al. or other flow detector measurer. The components generally include a laser diode, a piano convex lens, spatial filter (attenuator), electrical circuitry for determining when a flaw exists, lens cleaner and air wipe plate, for example, the particulars of which are more fully described in U.S. Pat. No. 5,436,719 to Doles et al. and are incorporated herein by reference. In this regard, the preferred light source 14 and detector measurer 16 utilize scattered light rays (in-plane scattered rays being removed and out-of-plane being detected). While the present invention employs the described light source 14 and detector measurer 16, other systems may be employed for this aspect of the invention. For example, refraction and diffraction light ray detection devices may be used.

The computer 12 has interface hardware and software in a microprocessor 12b to receive and manipulate signals from the detector measurer 16, such as that provided with the Model 360 from Laser Mike, Inc. of Dayton, Ohio. The microprocessor 12b is operably associated with a capstan 23 which has a counter operably associated therewith such that the line speed and tracking of the optic fiber 100 can be calculated. The detector measurer 16 sends a signal to the computer 12b which in turn manipulates the signal to produce an output indicative of one of a normal area and flawed area of the optic fiber 100. Microprocessor 12b includes software and hardware to track the line speed and calculate the delay in time ($\Delta t$) when the flaw will pass the camera 18 and provide the microprocessor 12b with the synchronization data necessary for initiating and stopping the light source 21 and camera 18. Another microprocessor unit 12a is operably associated with the microprocessors 12b and camera 18. Here, microprocessor 12a is operatively associated with a keyboard 12d for entering and transmitting data to microprocessor 12b necessary for controlling operating parameters of light sources 14 and 21, measurer detector 16 and camera 18. The microprocessor 12a also receives and stores in memory 12c data from microprocessors 12b such as number of flaws in the optic fiber 100 and the distance and location of such flaws. The microprocessor 12a receives visual data signals from camera 18 and manipulates the same in conjunction with other received data from the microprocessors 12b and provides an output for visual display of the character and size of flaw in the optic fiber 100. A display 12e is operably associated with the microprocessor 12a to display the visual output.

The camera 18 is preferably of a high speed nature, for example a CLM 10 from Costar which can record at speeds up to 30 frames per second and stop motion for 1.2 microseconds and qualify a 5$\mu$ flaw. The computer 12 includes software in which to communicate with the camera 18, for example, and an RS170 to interface to CVA-M10 camera and which initiates the camera 18 to record the flawed area upon producing an output indicative of a flawed area. Also, the computer 12 can be programmed to look at a predetermined window size generated by the camera 18, a 1.5 mm×1.5 mm, for example, to further ascertain the type and characterize the nature of the fiber 100 and flawed area. The light source 21 is a strobe light or plurality of LEDs which are capable of generating a wide beam of light at the optic fiber 100.

Preferably there are two cameras 18a and 18b and two light sources 21a and 21b. A first light source 21a is at a position to illuminate the optic fiber 100 and a second light source 21b is in a generally common plane at a position substantially 90° from the first light source 21a to further illuminate the optic fiber 100. A first camera 18a is in a generally common plane positioned substantially 180° from the first light source 21a to receive light illuminated about the optic fiber 100 and generate a signal indicative of the visual character of the optic fiber 100 and a second camera 18a is in a generally common plane positioned substantially 180° from the second light source 18b to also receive light illuminated about the optic fiber 100 and generate another signal indicative of the visual character of the optic fiber 100. These signals are utilized as described herein by the microprocessor 12b to provide greater coverage of the fiber 100.

Several principles are utilized in the invention. The camera 18 is fixed at a predetermined distance $\Delta x$ down line from the detector 16. The optic fiber 100 is formed and meteringly drawn from the tower 22 onto a spool 20 at a line speed $\Delta x/\Delta t$ which can vary. From this, the time it takes for a point on the optic fiber 100 to travel from the light source 14/detector 16 to the light source 21/camera 18 is a calculable number t3 and is a function of variable line speed.

As the optic fiber 100 moves past the light source 14/detector 16 and a flawed area is detected, the computer 12 stores this at time t1. When the flaw is no longer detected, the computer 12 stores this at time t2. The time change $\Delta t$ is calculated as t2−t1 and the computer 12 initiates the light source 21 and camera 18 such that images are recorded for a predetermined period of about 1 $\mu$s, for example, to freeze the motion of the fiber. Initiation of the light source 21 at t3 and camera 18 can vary $\Delta t$ to capture different segments of the flaw as selected by computer 12 and light source 14/detector 16. Greater periods of exposure can be used dependent on line speed. It is noted that in the preferred embodiment, a pulse of light is provided at the beginning of the flaw and at the end of the flaw.

With respect to the timing of the flaw capture, the following points are to be noted. Line speed is maintained and recorded by the computer 12 either by direct input via a keyboard, operable connection tachometer or another computer. Line speed is represented by $\Delta x/\Delta t=(x2-x1)/(t2-t1)$. The time at detection of flaw is t1 and has a coordinate position of x1. The time to capture the flaw is t2 and has a coordinate position of x2. The distance from detection to recording the flaw is $\Delta x1$. The time for triggering the camera 18 is $t2=(\Delta x1)/(\Delta x/\Delta t)+t1$.

The optic fiber 100 can be unwound to the exact point where the flawed area was detected by virtue of the metered record and the footage viewed to ascertain the character and size of the flawed area. Once analyzed, the flawed area can removed in accordance with conventional techniques with the advantage herein provided by removing only that amount of fiber needed in which to remove the flawed area. No excess fiber need be removed as before where guesswork led to waste in overcompensating for the uncertainty as to the flawed area's nature and size.

The above described embodiments are set forth by way of example and are not for the purpose of limiting the present invention. It will be readily apparent to those skilled in the art that obvious modifications, derivations and variations can be made to the embodiments without departing from the scope of the invention. Accordingly, the claims appended hereto should be read in their full scope including any such modifications, derivations and variations.

What is claimed is:

1. A device for use in detecting, characterizing and correcting flaws in optic fibers which is formed at continuous and variable line speeds, comprising:

a light source for generating a beam of light at an optic fiber;

means for detectably measuring at least one of refracted light rays, diffracted light rays and scattered light rays from said beam and generating a signal in response thereto;

camera means for visually recording the flawed area in the optic fiber; and a computer based device operatively associated with said detector means and said camera means and having means for receiving said signal and manipulating said signal to produce an output indicating one of a normal area and a flawed area and further having means for continuously sensing line speed of the optic fiber, means for adjustably controlling said camera means in response to said output and said sensed line speed causing said camera means to visual recording the flawed area in accordance therewith.

2. The device for use in detecting, characterizing and correcting flaws in optic fibers of claim 1, wherein said camera means includes at least one light source and at least one high speed camera having a record speed up to thirty frames per second.

3. The device for use in detecting, characterizing and correcting flaws in optic fibers of claim 1, wherein said computer based device includes means for visually displaying said recording.

4. The device for use in detecting, characterizing and correcting flaws in optic fibers of claim 1, which further includes means for meteringly tracking the flawed areas to permit removal thereof.

5. The device for use in detecting, characterizing and correcting flaws in optic fibers of claim 2, which includes a first light source at a first position to illuminate the optic fiber, a second light source positioned in a generally common plane substantially 90° from said first light source to illuminate the optic fiber, a first camera positioned in a generally common plane substantially 180° from said first light source to receive light illuminated about the optic fiber and a second camera positioned in a generally common plane substantially 180° from said second light source to receive light illuminated about the optic fiber.

6. A method for use in detecting, characterizing and correcting flaws in an optic fiber which is formed at continuous and variable line speeds, which includes the steps of:

(A) directing a beam of light at an optic fiber;

(B) detecting at least one of refracted light rays, diffracted light rays and scattered light rays from said beam and generating a signal in response thereto;

(C) employing camera means for recording the flawed area in response to the indication of the flawed area;

(D) employing a computer-based device for receiving the signal and manipulating the signal to produce and output indicative of one of a normal area and a flawed area and further having means for sensing variable line speed of the optic fiber, means for adjustably controllably initiating said camera means in response to said output and said sensed line speed causing said camera means to visual recording the flawed area in accordance therewith.

7. The method of claim 6, which further includes the step of displaying the flawed area.

8. The method of claim 7, which further includes the step of removing the flawed area from the fiber.

* * * * *